(12) United States Patent
Pedro et al.

(10) Patent No.: US 11,324,909 B2
(45) Date of Patent: *May 10, 2022

(54) VENTILATION MASK

(71) Applicant: Revolutionary Medical Devices, Inc., Tucson, AZ (US)

(72) Inventors: Michael J. Pedro, Brooklyn, NY (US); Steven H. Cataldo, New York, NY (US); David M. Kane, Tucson, AZ (US); Thomas Reilly, Tucson, AZ (US); Ryan Redford, Tucson, AZ (US)

(73) Assignee: Revolutionary Medical Devices, Inc., Tucson, AZ (US)

(*) Notice: Subject to any disclaimer, the term of this patent is extended or adjusted under 35 U.S.C. 154(b) by 408 days.

This patent is subject to a terminal disclaimer.

(21) Appl. No.: 16/375,737

(22) Filed: Apr. 4, 2019

(65) Prior Publication Data

US 2019/0232012 A1   Aug. 1, 2019

Related U.S. Application Data

(63) Continuation of application No. 15/272,160, filed on Sep. 21, 2016, now Pat. No. 10,252,016, which is a (Continued)

(51) Int. Cl.
*A61M 16/06* (2006.01)
*A61M 16/01* (2006.01)
(Continued)

(52) U.S. Cl.
CPC ......... *A61M 16/0683* (2013.01); *A61B 5/082* (2013.01); *A61B 5/097* (2013.01);
(Continued)

(58) Field of Classification Search
CPC .............. A61M 16/085; A61M 16/201; A61M 16/0078; A61M 16/22; A61M 16/0683;
(Continued)

(56) References Cited

U.S. PATENT DOCUMENTS 1,050,621 A    1/1913   Ford
1,131,802 A    3/1915   Stenshoel
(Continued)

FOREIGN PATENT DOCUMENTS

CA    2363900 A1    5/2003
CN    202478364     10/2012
(Continued)

OTHER PUBLICATIONS

Australian Office Action for Application No. 2020204637, dated Mar. 26, 2021, 5 pages.

(Continued)

*Primary Examiner* — Margaret M Luarca
(74) *Attorney, Agent, or Firm* — Morgan, Lewis & Bockius LLP

(57) ABSTRACT

Disclosed is a nasal ventilation mask having separate ports to monitor end-tidal $CO_2$ expulsion integrated into the mask in order to monitor end-tidal $CO_2$ expelled nasally or orally. Also disclosed is a CPR mask for nose-to-mouth and/or mouth-to-mouth resuscitation, having a body shaped to cover the nose and/or mouth of a victim, the mask including a $CO_2$ absorber for eliminating at least in part rescuer's exhaled $CO_2$ delivered to the victim.

20 Claims, 9 Drawing Sheets

Related U.S. Application Data continuation of application No. 15/127,758, filed as application No. PCT/US2015/044341 on Aug. 7, 2015, now abandoned.

(60) Provisional application No. 62/161,041, filed on May 13, 2015, provisional application No. 62/078,677, filed on Nov. 12, 2014, provisional application No. 62/039,759, filed on Aug. 20, 2014.

(51) Int. Cl.
| | |
|---|---|
| *A61M 16/10* | (2006.01) |
| *A61M 16/20* | (2006.01) |
| *A61M 16/22* | (2006.01) |
| *A61M 16/08* | (2006.01) |
| *A61B 5/08* | (2006.01) |
| *A61B 5/097* | (2006.01) |
| *A61M 16/00* | (2006.01) |

(52) U.S. Cl.
CPC ...... *A61M 16/0003* (2014.02); *A61M 16/009* (2013.01); *A61M 16/0048* (2013.01); *A61M 16/0078* (2013.01); *A61M 16/0093* (2014.02); *A61M 16/01* (2013.01); *A61M 16/06* (2013.01); *A61M 16/0605* (2014.02); *A61M 16/0694* (2014.02); *A61M 16/085* (2014.02); *A61M 16/1055* (2013.01); *A61M 16/201* (2014.02); *A61M 16/208* (2013.01); *A61M 16/22* (2013.01); *A61M 2202/0208* (2013.01); *A61M 2202/0241* (2013.01); *A61M 2205/0238* (2013.01); *A61M 2210/0618* (2013.01); *A61M 2230/432* (2013.01)

(58) Field of Classification Search
CPC ............ A61M 16/009; A61M 16/0048; A61M 16/01; A61M 16/06; A61B 5/097
See application file for complete search history.

(56) References Cited

U.S. PATENT DOCUMENTS

| | | |
|---|---|---|
| 1,441,817 A | 1/1923 | McCullough |
| 1,729,525 A | 9/1929 | Stenshoel |
| 1,776,167 A | 9/1930 | Stenshoel |
| 2,452,816 A | 11/1948 | Wagner |
| 2,843,121 A | 7/1958 | Hudson |
| 2,939,458 A | 6/1960 | Lundquist |
| 3,013,556 A | 12/1961 | Galleher |
| 3,522,612 A | 8/1970 | Palmer |
| 3,556,097 A | 1/1971 | Wallace |
| 3,799,164 A | 3/1974 | Rollins |
| 3,815,596 A | 6/1974 | Keener et al. |
| 3,856,051 A | 12/1974 | Bain |
| 3,889,668 A | 6/1975 | Ochs et al. |
| 3,897,777 A | 8/1975 | Morrison |
| D242,490 S | 11/1976 | Belkin |
| 4,005,499 A | 2/1977 | Klein |
| 4,007,737 A | 2/1977 | Paluch |
| 4,015,598 A | 4/1977 | Brown |
| 4,188,946 A | 2/1980 | Watson et al. |
| D256,161 S | 7/1980 | Oliver |
| 4,231,363 A | 11/1980 | Grimes |
| 4,232,667 A | 11/1980 | Chalon et al. |
| 4,248,218 A | 2/1981 | Fischer |
| 4,259,757 A | 4/1981 | Watson |
| 4,265,235 A | 5/1981 | Fukunaga |
| 4,265,239 A * | 5/1981 | Fischer, Jr. ......... A61M 16/009 128/205.17 |
| 4,275,720 A | 6/1981 | Wichman |
| 4,328,797 A | 5/1982 | Rollins |
| 4,457,026 A | 7/1984 | Morris |
| 4,463,755 A | 8/1984 | Suzuki |
| 4,471,769 A | 9/1984 | Lockhart |
| 4,574,796 A | 3/1986 | Lundstrom |
| 4,596,246 A | 6/1986 | Lyall |
| 4,657,010 A | 4/1987 | Wright |
| 4,700,691 A | 10/1987 | Tari et al. |
| 4,770,169 A | 9/1988 | Schmoegner et al. |
| 4,905,712 A | 3/1990 | Bowlin et al. |
| 5,046,200 A | 9/1991 | Feder |
| 5,046,491 A | 9/1991 | Derrick |
| 5,121,746 A | 6/1992 | Sikora |
| D333,404 S | 2/1993 | Thompson |
| 5,220,699 A | 6/1993 | Farris |
| 5,243,971 A | 9/1993 | Sullivan et al. |
| 5,255,303 A | 10/1993 | DiMaio et al. |
| 5,271,390 A | 12/1993 | Gray et al. |
| 5,284,160 A | 2/1994 | Dryden |
| D347,494 S | 5/1994 | Mustelier |
| D354,128 S | 1/1995 | Rinehart |
| 5,404,873 A | 4/1995 | Leagre et al. |
| 5,462,050 A | 10/1995 | Dahlstrand |
| 5,474,060 A | 12/1995 | Evans |
| 5,485,837 A | 1/1996 | Solesbee et al. |
| 5,524,639 A | 6/1996 | Lanier et al. |
| D373,921 S | 9/1996 | Palomo et al. |
| 5,557,049 A | 9/1996 | Ratner |
| RE35,339 E | 10/1996 | Rapoport |
| 5,560,354 A | 10/1996 | Berthon-Jones et al. |
| 5,586,551 A | 12/1996 | Hilliard |
| 5,647,357 A | 7/1997 | Barnett et al. |
| 5,649,331 A | 7/1997 | Wilkinson et al. |
| 5,660,174 A | 8/1997 | Jacobelli |
| 5,661,859 A | 9/1997 | Schaefer |
| 5,685,298 A | 11/1997 | Idris |
| 5,738,094 A | 4/1998 | Hoftman |
| 5,746,201 A | 5/1998 | Kidd |
| 5,749,358 A | 5/1998 | Good et al. |
| 5,778,872 A | 7/1998 | Fukunaga et al. |
| D402,755 S | 12/1998 | Kwok |
| 5,884,624 A | 3/1999 | Barnett et al. |
| 5,933,886 A | 8/1999 | Washington |
| 5,960,494 A | 10/1999 | Gilliland |
| 5,966,763 A | 10/1999 | Thomas et al. |
| 5,975,079 A | 11/1999 | Hellings et al. |
| 5,983,896 A | 11/1999 | Fukunaga et al. |
| 6,003,511 A | 12/1999 | Fukunaga et al. |
| 6,019,101 A | 2/2000 | Cotner et al. |
| 6,035,852 A | 3/2000 | Hoftman |
| 6,058,933 A | 5/2000 | Good et al. |
| D428,987 S | 8/2000 | Kwok |
| 6,112,746 A | 9/2000 | Kwok et al. |
| 6,123,071 A | 9/2000 | Berthon-Jones et al. |
| 6,129,082 A | 10/2000 | Leagre |
| 6,152,137 A | 11/2000 | Schwartz et al. |
| D435,650 S | 12/2000 | Kwok |
| 6,192,886 B1 | 2/2001 | Rudolph |
| 6,216,691 B1 | 4/2001 | Kenyon et al. |
| 6,263,874 B1 * | 7/2001 | LeDez ................ A61M 16/009 128/205.25 |
| 6,342,040 B1 | 1/2002 | Starr et al. |
| 6,357,441 B1 | 3/2002 | Kwok et al. |
| 6,397,847 B1 | 6/2002 | Scarberry et al. |
| 6,401,713 B1 | 6/2002 | Hill et al. |
| 6,412,487 B1 | 7/2002 | Gunaratnam et al. |
| 6,412,488 B1 | 7/2002 | Barnett et al. |
| 6,439,230 B1 | 8/2002 | Gunaratnam et al. |
| 6,439,231 B1 | 8/2002 | Fukunaga et al. |
| 6,446,288 B1 | 9/2002 | Pi |
| 6,459,923 B1 | 10/2002 | Plewes et al. |
| 6,463,931 B1 | 10/2002 | Kwok et al. |
| 6,467,483 B1 | 10/2002 | Kopacko et al. |
| D467,345 S | 12/2002 | Gingles et al. |
| 6,513,526 B2 | 2/2003 | Kwok et al. |
| 6,520,182 B1 | 2/2003 | Gunaratnam et al. |
| 6,581,602 B2 | 6/2003 | Kwok |
| 6,584,977 B1 | 7/2003 | Serowski |
| 6,612,306 B1 | 9/2003 | Mault |
| 6,615,835 B1 | 9/2003 | Cise |
| 6,626,178 B2 | 9/2003 | Morgan et al. |
| 6,645,835 B1 | 9/2003 | Cise |

(56) References Cited

U.S. PATENT DOCUMENTS

| | | |
|---|---|---|
| 6,631,713 B1 | 10/2003 | Christopher |
| 6,631,718 B1 | 10/2003 | Lovell |
| 6,634,358 B2 | 10/2003 | Kwok et al. |
| 6,651,663 B2 | 11/2003 | Barnett et al. |
| 6,694,973 B1 | 2/2004 | Dunhao et al. |
| 6,701,927 B2 | 3/2004 | Kwok et al. |
| 6,729,333 B2 | 5/2004 | Barnett et al. |
| 6,736,139 B1 | 5/2004 | Wix |
| D493,523 S | 7/2004 | Barnett et al. |
| 6,779,524 B2 | 8/2004 | Strawder et al. |
| 6,792,943 B2 | 9/2004 | Kumar et al. |
| 6,796,308 B2 | 9/2004 | Gunaratnam et al. |
| 6,805,117 B1 | 10/2004 | Ho et al. |
| 6,832,610 B2 | 12/2004 | Gradon et al. |
| 6,863,071 B2 | 3/2005 | Annett et al. |
| 6,871,649 B2 | 3/2005 | Kwok et al. |
| 6,892,729 B2 | 5/2005 | Smith et al. |
| 6,895,965 B2 | 5/2005 | Scarberry et al. |
| 6,931,664 B1 | 8/2005 | Chen |
| 6,935,337 B2 | 8/2005 | Virr et al. |
| 6,981,503 B1 | 1/2006 | Shapiro |
| 7,004,168 B2 | 2/2006 | Mace et al. |
| 7,007,696 B2 | 3/2006 | Palkon et al. |
| 7,013,896 B2 | 3/2006 | Schmidt |
| 7,017,576 B2 | 3/2006 | Olsen et al. |
| 7,021,311 B2 | 4/2006 | Gunaratnam et al. |
| 7,028,981 B2 | 4/2006 | Horton |
| 7,036,508 B2 | 5/2006 | Kwok |
| 7,047,971 B2 | 5/2006 | Ho et al. |
| 7,066,179 B2 | 6/2006 | Eaton et al. |
| 7,069,932 B2 | 7/2006 | Eaton et al. |
| 7,069,933 B2 | 7/2006 | Kwok et al. |
| 7,114,498 B1 | 10/2006 | Nashed |
| 7,159,587 B2 | 1/2007 | Drew et al. |
| 7,178,524 B2 | 2/2007 | Noble |
| 7,178,527 B2 | 2/2007 | Kwok et al. |
| 7,210,481 B1 | 5/2007 | Lovell et al. |
| 7,219,669 B1 | 5/2007 | Lovell et al. |
| 7,237,551 B2 | 7/2007 | Ho et al. |
| 7,243,651 B2 | 7/2007 | Kwok et al. |
| 7,287,528 B2 | 10/2007 | Ho et al. |
| 7,341,060 B2 | 3/2008 | Ging et al. |
| 7,383,839 B2 | 6/2008 | Porat et al. |
| 7,445,602 B2 | 11/2008 | Yamamori |
| 7,448,386 B2 | 11/2008 | Ho et al. |
| 7,467,431 B2 | 12/2008 | Weedling et al. |
| 7,487,772 B2 | 2/2009 | Ging et al. |
| 7,487,777 B2 | 2/2009 | Gunaratnam et al. |
| 7,500,280 B2 | 3/2009 | Dixon et al. |
| 7,500,482 B2 | 3/2009 | Biederman |
| 7,614,398 B2 | 11/2009 | Virr et al. |
| 7,631,644 B2 | 12/2009 | Ho et al. |
| 7,665,464 B2 | 2/2010 | Kopacko et al. |
| 7,669,599 B2 | 3/2010 | Gunaratnam et al. |
| 7,700,129 B2 | 4/2010 | Ito et al. |
| 7,743,767 B2 | 6/2010 | Ging et al. |
| 7,753,051 B2 | 7/2010 | Burrow et al. |
| 7,779,832 B1 | 8/2010 | Ho |
| 7,841,988 B2 | 11/2010 | Yamamori |
| 7,870,859 B2 | 1/2011 | Barnett et al. |
| 7,874,292 B2 | 1/2011 | Smith et al. |
| 7,913,337 B1 | 3/2011 | Masson |
| 7,926,487 B2 | 4/2011 | Drew et al. |
| 7,927,285 B2 | 4/2011 | Yamamori |
| 7,931,024 B2 | 4/2011 | Ho et al. |
| 7,938,117 B2 | 5/2011 | Chiesa et al. |
| 7,950,392 B2 | 5/2011 | Kwok et al. |
| 7,975,694 B2 | 7/2011 | Ho |
| 7,997,267 B2 | 8/2011 | Ging et al. |
| 8,001,968 B2 | 8/2011 | Doty et al. |
| 8,001,970 B2 | 8/2011 | King et al. |
| 8,028,699 B2 | 10/2011 | Ho et al. |
| 8,042,539 B2 | 10/2011 | Chandran et al. |
| 8,042,541 B2 | 10/2011 | Amarasinghe et al. |
| 8,056,561 B2 | 11/2011 | Kwok et al. |
| 8,132,270 B2 | 3/2012 | Lang et al. |
| 8,161,971 B2 | 4/2012 | Jaffe |
| 8,191,553 B2 | 6/2012 | Haworth et al. |
| 8,210,181 B2 | 7/2012 | Gunaratnam et al. |
| 8,261,745 B2 | 9/2012 | Chandran et al. |
| 8,261,746 B2 | 9/2012 | Lynch et al. |
| 8,267,091 B2 | 9/2012 | Smith et al. |
| 8,302,224 B2 | 11/2012 | Lehman |
| 8,312,883 B2 | 11/2012 | Gunaratnam et al. |
| 8,336,142 B1 | 12/2012 | See et al. |
| 8,336,549 B2 | 12/2012 | Nashed |
| 8,347,889 B2 | 1/2013 | Farnum |
| 8,365,734 B1 | 2/2013 | Lehman |
| 8,397,724 B2 | 3/2013 | Sher et al. |
| D681,383 S | 5/2013 | Derman et al. |
| 8,443,807 B2 | 5/2013 | McAuley et al. |
| 8,485,190 B2 | 7/2013 | Barnett et al. |
| 8,485,192 B2 | 7/2013 | Davidson et al. |
| 8,490,623 B2 | 7/2013 | Berthon-Jones et al. |
| RE44,453 E | 8/2013 | Virr et al. |
| 8,479,726 B2 | 9/2013 | McAuley |
| 8,522,783 B2 | 9/2013 | Kwok et al. |
| 8,528,558 B2 | 9/2013 | Drew et al. |
| 8,539,953 B2 | 9/2013 | Moenning, Jr. |
| 8,550,081 B2 | 10/2013 | Davidson et al. |
| 8,550,082 B2 | 10/2013 | Davidson et al. |
| 8,550,083 B2 | 10/2013 | Davidson et al. |
| 8,555,885 B2 | 10/2013 | Davidson et al. |
| 8,567,402 B2 | 10/2013 | Gunaratnam et al. |
| 8,567,404 B2 | 10/2013 | Davidson et al. |
| D693,603 S | 11/2013 | Esquivel et al. |
| 8,573,211 B2 | 11/2013 | Ho et al. |
| 8,573,212 B2 | 11/2013 | Lynch et al. |
| 8,573,213 B2 | 11/2013 | Davidson et al. |
| 8,573,214 B2 | 11/2013 | Davidson et al. |
| 8,573,215 B2 | 11/2013 | Davidson et al. |
| 8,573,217 B2 | 11/2013 | Todd et al. |
| 8,578,935 B2 | 11/2013 | Davidson et al. |
| 8,578,939 B1 | 11/2013 | Kimani Mwangi et al. |
| 8,613,280 B2 | 12/2013 | Davidson et al. |
| 8,613,281 B2 | 12/2013 | Davidson et al. |
| 8,616,211 B2 | 12/2013 | Davidson et al. |
| 8,631,792 B2 | 1/2014 | Ho et al. |
| 8,636,006 B2 | 1/2014 | Kwok et al. |
| 8,667,965 B2 | 3/2014 | Gunaratnam et al. |
| 8,684,004 B2 | 4/2014 | Eifler |
| 8,689,366 B2 | 4/2014 | Ho |
| 8,707,950 B1 | 4/2014 | Rubin |
| 8,714,157 B2 | 5/2014 | McAuley et al. |
| 8,752,551 B2 | 6/2014 | Chandran et al. |
| 8,807,134 B2 | 8/2014 | Ho et al. |
| 8,807,135 B2 | 8/2014 | Worboys et al. |
| 8,813,748 B2 | 8/2014 | Kwok et al. |
| 8,881,728 B2 | 11/2014 | Sher et al. |
| 8,915,861 B2 | 12/2014 | Yamamori et al. |
| 8,939,151 B2 | 1/2015 | McAuley et al. |
| 8,944,061 B2 | 2/2015 | D'Souza et al. |
| D726,303 S | 4/2015 | Rollins |
| 9,010,330 B2 | 4/2015 | Barlow et al. |
| 9,010,331 B2 | 4/2015 | Lang et al. |
| 9,022,029 B2 | 5/2015 | Varga et al. |
| 9,027,556 B2 | 5/2015 | Ng et al. |
| 9,138,169 B2 | 9/2015 | Beard |
| 9,186,474 B1 | 11/2015 | Rollins |
| 9,295,799 B2 | 3/2016 | McAuley et al. |
| 9,295,800 B2 | 3/2016 | Davidson et al. |
| D753,287 S | 4/2016 | Darab |
| D753,816 S | 4/2016 | Beard |
| 9,375,545 B2 | 6/2016 | Darkin et al. |
| 2002/0074001 A1 | 6/2002 | Kwok et al. |
| 2002/0174868 A1 | 11/2002 | Kwok et al. |
| 2003/0024533 A1 | 2/2003 | Sniadach |
| 2003/0145859 A1 | 8/2003 | Bohn et al. |
| 2003/0183232 A1 | 10/2003 | Fukunaga et al. |
| 2004/0069306 A1 | 4/2004 | Moenning |
| 2004/0221850 A1 | 11/2004 | Ging et al. |
| 2004/0261800 A1 | 12/2004 | Frank |
| 2005/0028811 A1 | 2/2005 | Nelson et al. |
| 2005/0145247 A1 | 7/2005 | Nashed |

(56) References Cited

U.S. PATENT DOCUMENTS

| | | |
|---|---|---|
| 2005/0160532 A1 | 7/2005 | Froelich |
| 2005/0193493 A1 | 9/2005 | Gabbay |
| 2006/0032500 A1 | 2/2006 | Ghiron et al. |
| 2006/0042631 A1 | 3/2006 | Martin et al. |
| 2006/0118117 A1 | 6/2006 | Berthon-Jones et al. |
| 2006/0124131 A1 | 6/2006 | Chandran et al. |
| 2006/0168730 A1 | 8/2006 | Menkedick et al. |
| 2006/0174889 A1 | 8/2006 | Noble |
| 2006/0231091 A1 | 10/2006 | Camarillo |
| 2006/0249160 A1 | 11/2006 | Scarberry |
| 2007/0062536 A1 | 3/2007 | McAuley et al. |
| 2007/0113847 A1 | 5/2007 | Acker et al. |
| 2007/0113856 A1 | 5/2007 | Acker et al. |
| 2007/0267017 A1 | 11/2007 | McAuley et al. |
| 2007/0271699 A1 | 11/2007 | Sacchetti |
| 2007/0295335 A1 | 12/2007 | Nashed |
| 2008/0053446 A1 | 3/2008 | Sleeper et al. |
| 2008/0092895 A1 | 4/2008 | Bimkrant |
| 2008/0092898 A1 | 4/2008 | Schneider et al. |
| 2008/0196715 A1 | 8/2008 | Yamamori |
| 2008/0221470 A1 | 9/2008 | Sather et al. |
| 2008/0230067 A1 | 9/2008 | Kwok et al. |
| 2009/0020127 A1 | 1/2009 | Boone et al. |
| 2009/0084385 A1 | 4/2009 | Lang |
| 2009/0114229 A1 | 5/2009 | Frater et al. |
| 2009/0114230 A1 | 5/2009 | Hernandez et al. |
| 2009/0133696 A1 | 5/2009 | Remmers et al. |
| 2009/0178680 A1 | 7/2009 | Chang |
| 2009/0250054 A1 | 10/2009 | Loncar |
| 2009/0250061 A1 | 10/2009 | Marasigan |
| 2009/0260628 A1 | 10/2009 | Flynn |
| 2009/0301472 A1 | 12/2009 | Kim |
| 2009/0320850 A1 | 12/2009 | Wallnewitz et al. |
| 2010/0122701 A1 | 5/2010 | Gunaratnam et al. |
| 2010/0122705 A1 | 5/2010 | Moenning, Jr. |
| 2010/0147313 A1 | 6/2010 | Albrecht |
| 2010/0170513 A1 | 7/2010 | Bowditch |
| 2010/0170516 A1 | 7/2010 | Grane |
| 2010/0218316 A1 | 9/2010 | Nissen et al. |
| 2010/0224199 A1 | 9/2010 | Smith et al. |
| 2010/0275919 A1 | 11/2010 | Sung |
| 2010/0313891 A1 | 12/2010 | Veliss et al. |
| 2011/0054366 A1 | 3/2011 | Smith et al. |
| 2011/0072582 A1 | 3/2011 | Patterson et al. |
| 2011/0083670 A1 | 4/2011 | Walacavage |
| 2011/0092930 A1 | 4/2011 | Poorman |
| 2011/0108035 A1 | 5/2011 | Samaniego |
| 2011/0114099 A1 | 5/2011 | Goldstein |
| 2011/0155136 A1 | 6/2011 | Lee |
| 2011/0173750 A1 | 7/2011 | Lehmann |
| 2011/0186050 A1 | 8/2011 | Daly |
| 2011/0214674 A1 | 9/2011 | Ging et al. |
| 2011/0220113 A1 | 9/2011 | Newman |
| 2011/0253150 A1 | 10/2011 | King |
| 2011/0265796 A1 | 11/2011 | Amarasinghe et al. |
| 2011/0290253 A1 | 12/2011 | McAuley et al. |
| 2012/0080035 A1 | 4/2012 | Guney et al. |
| 2012/0111330 A1 | 5/2012 | Gartner |
| 2012/0144588 A1 | 6/2012 | Heimbrock et al. |
| 2012/0180220 A1 | 7/2012 | Popitz |
| 2012/0222680 A1 | 9/2012 | Eves et al. |
| 2012/0227736 A1 | 9/2012 | Bowsher |
| 2012/0234326 A1 | 9/2012 | Mazzone et al. |
| 2012/0247475 A1 | 10/2012 | Hernandez et al. |
| 2012/0285455 A1 | 11/2012 | Varga et al. |
| 2012/0285466 A1 | 11/2012 | Pierro et al. |
| 2013/0014760 A1 | 1/2013 | Matula, Jr. et al. |
| 2013/0023729 A1 | 1/2013 | Vazales |
| 2013/0060157 A1 | 3/2013 | Beard |
| 2013/0109992 A1 | 5/2013 | Guyette |
| 2013/0146060 A1 | 6/2013 | Ho et al. |
| 2013/0186413 A1 | 7/2013 | Haines et al. |
| 2013/0190643 A1 | 7/2013 | Brambilla |
| 2013/0192601 A1 | 8/2013 | Reischl et al. |
| 2013/0192602 A1 | 8/2013 | Leibitzki et al. |
| 2013/0199537 A1 | 8/2013 | Formica et al. |
| 2013/0319417 A1 | 12/2013 | Weinman |
| 2014/0076311 A1 | 3/2014 | Darab |
| 2014/0083425 A1 | 3/2014 | Moenning, Jr. |
| 2014/0144448 A1 | 5/2014 | Eifler |
| 2014/0158135 A1 | 6/2014 | Shyong |
| 2014/0158136 A1 | 6/2014 | Romagnoli et al. |
| 2014/0215687 A1 | 8/2014 | Andrews |
| 2014/0243600 A1 | 8/2014 | Eisenberger |
| 2014/0243698 A1 | 8/2014 | Koch |
| 2014/0245537 A1 | 9/2014 | Allen |
| 2014/0251333 A1 | 9/2014 | Burk |
| 2014/0276178 A1 | 9/2014 | Simon |
| 2014/0326246 A1 | 11/2014 | Chodkowski et al. |
| 2014/0352072 A1 | 12/2014 | Holladay |
| 2014/0360504 A1 | 12/2014 | Kwok |
| 2015/0047647 A1 | 2/2015 | Winer |
| 2015/0059759 A1 | 3/2015 | Frater et al. |
| 2015/0144140 A1 | 5/2015 | Eury |
| 2015/0151070 A1 | 6/2015 | Capra |
| 2015/0217075 A1 | 8/2015 | Nair |
| 2015/0238716 A1 | 8/2015 | Budhiraja et al. |
| 2015/0250970 A1 | 9/2015 | Bowsher |
| 2015/0250971 A1 | 9/2015 | Bachelder et al. |
| 2015/0273170 A1 | 10/2015 | Bachelder et al. |
| 2015/0273171 A1 | 10/2015 | Sullivan et al. |
| 2015/0335852 A1 | 11/2015 | Miller |
| 2016/0015923 A1 | 1/2016 | Chodkowski et al. |
| 2016/0022944 A1 | 1/2016 | Chodkowski et al. |
| 2016/0038709 A1 | 2/2016 | Beard |
| 2016/0067441 A1 | 3/2016 | Bearne et al. |
| 2016/0151222 A1 | 6/2016 | Pedro |
| 2016/0184540 A1 | 6/2016 | Kokko |
| 2016/0213871 A1 | 7/2016 | Darab |
| 2016/0279368 A1 | 9/2016 | Isenberg |

FOREIGN PATENT DOCUMENTS

| | | |
|---|---|---|
| CN | 202505937 | 10/2012 |
| CN | 103153378 A | 6/2013 |
| DE | 19947722 | 4/2001 |
| EP | 2433666 | 3/2012 |
| GB | 187863 | 11/1922 |
| GB | 2209950 A | 6/1989 |
| GB | 2456136 | 7/2009 |
| JP | H02502161 A | 7/1990 |
| JP | H05507004 | 10/1993 |
| JP | 2005318975 A | 11/2005 |
| JP | 2007181661 A | 7/2007 |
| JP | 2008511399 A | 4/2008 |
| JP | 3192368 U | 8/2014 |
| JP | 2019103858 A | 6/2019 |
| WO | WO-2010059592 | 5/2010 |
| WO | WO-2012106373 A2 | 8/2012 |
| WO | WO-2013036839 | 3/2013 |
| WO | WO-2013064950 | 5/2013 |
| WO | WO-2013142909 A1 | 10/2013 |
| WO | WO-2014038959 | 3/2014 |
| WO | WO-2014210606 | 12/2014 |
| WO | WO-2015063283 | 5/2015 |
| WO | WO-2015131262 | 9/2015 |
| WO | WO-2015147947 | 10/2015 |
| WO | WO-2015187995 | 12/2015 |
| WO | WO-2016007749 | 1/2016 |
| WO | WO-2016097948 | 6/2016 |

OTHER PUBLICATIONS

Extended European Search Report for Application No. 211607098, dated Apr. 22, 2021, 7 pages.
Japanese Office Action for Application No. 2019041441, dated Feb. 4, 2020, 20 pages.
Japanese Office Action for Application No. 2019041441, dated Aug. 25, 2020, 6 pages.
Australian Office Action for Application No. 2015305893, dated Mar. 21, 2020, 5 pages.
Australian Certificate of Registration issued in application No. 201512961, dated Aug. 7, 2015, 5 pages.

(56) References Cited

OTHER PUBLICATIONS

Australian Certificate of Registration issued in application No. 201512962, dated Aug. 11, 2015, 5 pages.
Ball et al., "Performance comparison of two anaesthetic facemasks", Anaesth Intensive Care, Apr. 2007, vol. 35, Issue 2, 226-9 (abstract only), 2 pages.
Canadian Office Action issued in Application No. 162891, dated Apr. 5, 2016, 1 page.
Canadian Office Action issued in Application No. 162891, dated Nov. 10, 2015, 7 pages.
Chinese Notification of Grant for Application No. 201530191921.6, dated Feb. 15, 2016, 12 pages.
Chinese Office Action (w/translation) for Application No. 201480042735.9, dated Apr. 5, 2017, 18 pages.
Chinese Office Action for Application No. 201480042735.9, dated Nov. 6, 2017, 21 pages.
Chinese Office Action for Application No. 201580029981.5, dated Sep. 5, 2018, 14 pages.
Chinese Office Action for Application No. 201730161613.8, dated Aug. 7, 2017, 2 pages.
Chinese Office Action for Application No. 201730161613.8, dated Sep. 19, 2017, 11 pages.
CPAP product description, http://www.cpap.com/productpage/pr-amara-full-face-cpap-mask-gel-silicone.html, downloaded Jul. 28, 2016, 11 pages.
CPAPXCHANGE product image, http://www.cpapexchange.com/cpap-masks-bipap-masks/bluegel-full-cushion-comfortgel-cpap-bipap-masks.jpg, downloade Jul. 28, 2016, 1 page.
DirectHome Medical product description, http://www.directhomemedical.com/profilelite-gel-cpap-mask-philipsrespironics.html#.VwXLIPkrLIU, downloaded Jul. 28, 2016, 6 pages.
English Translation of Japanese Office Action for Application No. 2016-005262, dated Jun. 30, 2016, 1 page.
English Translation of Japanese Office Action for Application No. 2016-005263, dated Jun. 30, 2016, 1 page.
European Office Action for Application No. 003933217-0001, dated May 16, 2017, 2 pages.
European Partial Supplementary European Search Report for Application No. 14818563.0, dated Jan. 30, 2017, 6 pages.
Extended European Search Report for Application No. 14818563.0, dated May 3, 2017, 12 pages.
Extended European Search Report for Application No. 15803670.7, dated Oct. 24, 2018, 12 pages.
Extended European Search Report for Application No. 15833101.7, dated Jul. 3, 2018, 13 pages.
Indian Office Action for Indian Design Patent Application No. 272704, dated Aug. 28, 2015, 13 pages.
InnoMed Technologies Sylent Mask product description, http://innomedinc.com/sylent-ne-disposable-nasal-mask/, downloaded Jul. 28, 2016, 2 pages.
InnoMed Technologies, Hybrid Mask product description, http://innomedinc.com/hybrid/, downloaded Jul. 28, 2016, 4 pages.
International Preliminary Report on Patentability for Application No. PCT/US2014/044934, dated Jan. 7, 2016, 12 pages.
International Preliminary Report on Patentability for Application No. PCT/US2015/021323, dated Oct. 6, 2016, 8 pages.
International Preliminary Report on Patentability for Application No. PCT/US2015/044341, dated Mar. 2, 2017, 10 pages.
International Preliminary Report on Patentability for Application No. PCT/US2016/037070, dated Dec. 12, 2017, 7 pages.
International Search Report and Written Opinion for Application No. PCT/US2017/048046, dated Nov. 6, 2017, 11 pages.
Invitation to Pay Additional Fees for Application No. PCT/US14/44934, dated Oct. 24, 2014, 3 pages.
Invitation to Pay Additional Fees for Application No. PCT/US15/44341, dated Oct. 21, 2015, 2 pages.
Israeli Notice of Allowance for Application No. 57056 (w/translation of relevant portions), dated Nov. 1, 2015, 3 pages.
Israeli Notice of Allowance for Applicatoin No. 57056 (no translation), dated May 29, 2016, 1 page.
Israeli Office Action for Application No. 57850 (w/translation of relevant portions), dated Feb. 14, 2016, 3 pages.
Israeli Office Action for Application No. 58250 (w/translation of relevant portions), dated Jun. 29, 2016, 2 pages.
Israeli Office Action issued in application No. 58250 (w/translation of relevant portions), dated Jul. 18, 2016, 3 pages.
Japanese Decision for Registration (w/translation) for Application No. 2016-006559, dated May 12, 2017, 2 pages.
Japanese Decision for Registration (w/translation) for Application No. 2016-006560, dated May 12, 2017, 2 pages.
Japanese Decision for Registration for Application No. 2016-005263, dated Dec. 22, 2017, 4 pages.
Japanese Decision for Registration for Application No. 2017-009813, dated Oct. 6, 2017, 2 pages.
Japanese Office Action (w/translation) for Application No. 2016-005262, dated Apr. 28, 2017, 7 pages.
Japanese Office Action (w/translation) for Application No. 2016-005263, dated Apr. 28, 2017, 7 pages.
Japanese Office Action (w/translation) for Application No. 2016-006559, dated Sep. 2, 2016, 3 pages.
Japanese Office Action (w/translation) for Application No. 2016-006560, dated Sep. 2, 2016, 3 pages.
Japanese Office Action for Application No. 2015-013148, dated Dec. 18, 2015, 3 pages.
Japanese Office Action for Application No. 2016-005262, dated Dec. 22, 2017, 4 pages.
Japanese Office Action for Application No. 2017-009813, dated Jul. 28, 2017, 3 pages.
Japanese Office Action for Application No. 2017-509724, dated Jul. 24, 2018, 12 pages.
Korean Design of Registration for Application No. 30-2015-0029561, M002 (w/translation), dated Jul. 27, 2016, 3 pages.
Korean Notice of Design of Registration for Application No. 30-2015-0029561, M001 (w/translation), dated Jun. 29, 2016, 3 pages.
Korean Office Action for Application No. 30-2015-0029561, M0001, dated Jun. 9, 2016, 16 pages.
Korean Office Action for Application No. 30-2015-0029561, M001 (w/translation), dated Dec. 24, 2015, 12 pages.
Korean Office Action for Application No. 30-2015-0029561, M001, dated May 23, 2016, 2 pages.
Korean Office Action for Application No. 30-2015-0029561, M002 (w/translation), dated Dec. 24, 2015, 7 pages.
Korean Office Action for Application No. 30-2015-0029561, M002 (w/translation), dated May 23, 2016, 6 pages.
Liang, Yafen et al., "Nasal Ventilation is More Effective than Combined Oral-Nasal Ventilation during Induction of General Anesthesia in Adult Subjects", Anesthesiology 2008, vol. 108, No. 6, Jun. 2008, pp. 998-1003.
Notice of Allowance (corrected) for U.S. Appl. No. 15/288,973, dated Feb. 10, 2017, 16 pages.
Notice of Allowance (corrected) for U.S. Appl. No. 15/288,973, dated Mar. 10, 2017, 9 pages.
Notice of Allowance (corrected) for U.S. Appl. No. 15/288,973, dated Mar. 24, 2017, 9 pages.
Notice of Allowance for U.S. Appl. No. 15/288,973, dated Feb. 1, 2017, 25 pages.
Notice of Decision of Registration for Design for Korean Design Application No. 30-20016-0014111, dated Dec. 13, 2016, 3 pages.
Office Action for U.S. Appl. No. 29/520,420, dated Aug. 11, 2016, 18 pages.
Office Action for U.S. Appl. No. 29/530,124, dated Aug. 12, 2016, 17 pages.
Office Action for U.S. Appl. No. 15/272,074, dated Apr. 19, 2017, 54 pages.
Office Action for U.S. Appl. No. 15/272,074, dated Jul. 31, 2017, 34 pages.
Office Action for U.S. Appl. No. 15/272,074, dated Sep. 13, 2017, 5 pages.
Office Action for U.S. Appl. No. 15/272,160, dated Apr. 24, 2017, 39 pages.
Office Action for U.S. Appl. No. 15/272,160, dated Dec. 15, 2017, 34 pages.

(56) References Cited

OTHER PUBLICATIONS

Office Action for U.S. Appl. No. 15/272,160, dated Jan. 4, 2017, 31 pages.
Office Action for U.S. Appl. No. 15/272,190, dated Dec. 28, 2017, 22 pages.
Office Action for U.S. Appl. No. 15/272,190, dated Jan. 30, 2017, 32 pages.
Office Action for U.S. Appl. No. 15/272,190, dated Jun. 21, 2017, 7 pages.
Office Action for U.S. Appl. No. 15/272,190, dated May 23, 2017, 36 pages.
Office Action for U.S. Appl. No. 15/288,973, dated Dec. 14, 2016, 21 pages.
Office Action for U.S. Appl. No. 29/520,420, dated Apr. 7, 2017, 3 pages.
Office Action for U.S. Appl. No. 29/520,420, dated Dec. 8, 2017, 5 pages.
Office Action for U.S. Appl. No. 29/520,420, dated Feb. 24, 2017, 14 pages.
Office Action for U.S. Appl. No. 29/520,420, dated Jun. 15, 2017, 12 pages.
Office Action for U.S. Appl. No. 29/530,124, dated Apr. 19, 2017, 6 pages.
Office Action for U.S. Appl. No. 29/530,124, dated Aug. 30, 2017, 3 pages.
Office Action for U.S. Appl. No. 29/530,124, dated Aug. 9, 2017, 11 pages.
Office Action for U.S. Appl. No. 29/530,124, dated Feb. 28, 2017, 16 pages.
Office Action for U.S. Appl. No. 29/530,124, dated Jun. 21, 2017, 14 pages.
Office Action for U.S. Appl. No. 29/530,124, dated Nov. 29, 2017, 31 pages.
Partial Supplementary European Search Report for Application No. 16808466.3, dated Jan. 22, 2019, 14 pages.
Singapore Invitation to Respond to Written Opinion for Application No. 11201610048P, dated Sep. 19, 2017, 16 pages.
Singapore Invitation to Respond to Written Opinion for Application No. 11201701253U, dated Nov. 8, 2017, 12 pages.
Singapore Search Report for Application No. 11201510589T, dated Jan. 31, 2017, 11 pages.
Sleep Medicine Solutions product description, Http://sleepmedicinesolutions.net.au/cpap-spare-parts/26-fisher-paykel-zest-foams.html, downloaded Jul. 28, 2016, 2 pages.
Sleepnet homepage, https://web.archive.org/web/20111021122613/http://www.sleepnetmasks.com/, downloaded Jul. 28, 2016, 4 pages.
Australian Office Action for Application No. 2015305893, dated Jun. 21, 2019, 5 pages.
Chinese Office Action for Application No. 201580044737.6, dated Jun. 20, 2019, 11 pages.
Canadian Office Action for Application No. 2958557, dated Oct. 6, 2021, 6 pages.
Mexican Office Action for Application No. MX/a/2017/000753, dated Sep. 2, 2021, 4 pages including machine translation.
New Zealand Office Action for Application No. 729942, dated Sep. 20, 2021, 3 pages.
Japanese Office Action for Application No. 2020-216060, dated Nov. 30, 2021, 10 pages including translation.
New Zealand Office Action for Application No. 766784, dated Dec. 14, 2021, 3 pages.

\* cited by examiner

VENTILATION MASK

CROSS-REFERENCE TO RELATED APPLICATIONS

This application is a continuation of U.S. patent application Ser. No. 15/272,160, filed Sep. 21, 2016, which is a continuation of U.S. patent application Ser. No. 15/127,758, filed Sep. 20, 2016, which in turn claims priority from PCT Patent Application Serial No. PCT/US2015/044341, filed Aug. 7, 2015, which claims priority from U.S. Provisional Application Ser. No. 62/039,759, filed Aug. 20, 2014, and from U.S. Provisional Application Ser. No. 62/078,677, filed Nov. 12, 2014, and from U.S. Provisional Application Ser. No. 62/161,041, filed May 13, 2015, the disclosure of each of which is incorporated herein by reference in its entirety.

BACKGROUND OF THE INVENTION

The present invention relates to improvements in anesthesia masks and ventilation masks.

During surgery a patient usually is placed under anesthesia. The most common delivery system consists of canisters containing anesthesia gases and oxygen, a system of regulating the gas flow and the patient's breathing, and a device ensuring the potency of the patient's airway for breathing, oxygenation and the delivery of the anesthetic gas mixture. A ventilation mask is used to provide oxygen to the patient either during emergency and/or elective airway management, which includes but is not limited to; before a patient is anesthetized for surgery, while the patient is anesthetized, if the patient is sedated during the surgery or procedure, while the patient is recovering from anesthesia, after the patient has recovered from anesthesia, or during any event where a patient requires supplemental oxygen. However, one of the drawbacks of mask ventilation is that it requires constant contact between the provider's hands and the patient's face to hold the mask in place and keep the patient in the sniffing position in order to ensure that oxygen and anesthetic gases do not leak out into the air and that the patient's airway remains patent. If the provider does not maintain the patient in the sniffing position, a dangerous complication known as upper airway obstruction may occur. The reason the provider needs to perform continuous mask holding and maneuvering is the human anatomy and physiology. When muscles of the jaw, tongue and upper airway relax due to sedatives and/or muscle relaxants given to the patient for sedation and/or anesthesia, the upper airway (mouth, pharynx, larynx) may become partially obstructed and possibly completely closed. Wherein, when the jaw of the patient drops and the tongue obstructs the airway resulting in snoring (partial obstruction) or apnea (complete inability for oxygen to pass via the upper airway into the lungs). Another problem exists when a provider fails to administer enough anesthesia or sedation or it begins to wear off and the patient begins to move. This can cause the patient's airway to obstruct as well since the patient's head and neck position are no longer in the sniffing position. Patient movement during surgery can also be dangerous because it can cause the surgeon to make a mistake, particularly in eye, ear, nose, neck, head, and throat surgery.

Furthermore, situations arise during surgery that require rapid intubation of a patient. Full face masks, i.e. masks covering both the nose and mouth of a patient are problematic in emergency situations since a mask must be removed to uncover the mouth of a patient for intubation. However, removing the mask also removes oxygen support. As will be described below, the present invention in one aspect addresses the aforesaid and other disadvantages of the prior art.

The present invention, in another aspect relates to cardiopulmonary resuscitation (CPR) masks.

Cardiopulmonary resuscitation, commonly known as CPR is an emergency procedure performed in an effort to manually preserve intact brain function until further measures may be taken to restore spontaneous blood circulation and breathing in a person (hereinafter the "subject" or "victim") who is in cardiac arrest. CPR also is indicated in those who are unresponsive with no breathing such as in the case of a drowning victim or victim of electrical shock, or abnormal breathing, for example agonol respiration.

CPR involves chest compressions at least two inches deep and at a rate of at least 100 per minute in an effort to create artificial circulation by manually pumping blood through the heart and thus the body. The rescuer also may provide breaths by either exhaling directly into the subject's mouth, or through a CPR mask into the subject's mouth and/or nose (collectively "mouth-to-mouth resuscitation"), or using a device that pushes air into the subject's lungs through the subject's mouth and/or nose. The process of externally providing ventilation is termed "artificial respiration". Current recommendations place emphasis on high-quality chest compressions over artificial respiration; however, when coupled with high-quality chest compressions, artificial respiration provides potentially the greatest benefit to the patient.

Conventional CPR masks are held in place by hand, by the CPR provider, or may be retained in position by straps that extend behind the head of the subject or victim. While CPR masks may assist in ventilation of a subject or victim who is not breathing, when a rescuer provides mouth-to-mouth and/or nose-to-mouth resuscitation, the air provided contains a significant amount of $CO_2$ which is lethal. As will be discussed below, the present invention in another aspect addresses the aforesaid and other disadvantages of the prior art.

SUMMARY OF THE INVENTION

The present invention in one aspect provides an improved ventilation/anesthesia mask that overcomes the aforesaid and other problems of the prior art. More particularly, there is provided a nasal ventilation/anesthesia mask comprising one or more offset gas openings to allow the provider to have a clear view of the mouth and airway during direct laryngoscopy and intubation, which consists of a ventilation port to supply oxygen and other gases during anesthesia via Non-Invasive Positive Pressure Ventilation (NIPPV) and which is connected to an anesthesia circuit which can measure end-tidal $CO_2$ from the nose, an oral opening port under the nose for scavenging anesthesia gases and end-tidal $CO_2$ that are expelled orally from the patient; a gas scavenging/end-tidal $CO_2$ port connected to a channel inside the mask that is isolated from the nasal cavity, and an oxygen port for supplying post op oxygen. Completing the mask are a plurality of tabs or eyelets, preferably three, or four, for strapping the mask to the patient's head or for tying the mask down to the operating table, e.g., in accordance with the teachings of our PCT application PCT/US14/44934 and on PCT application PCT/US15/34277.

In one embodiment of the invention there is provided a nasal ventilation mask having an $O_2$ port for introducing oxygen into the mask, a ventilation port and a gas monitoring attachment integral to or attached to the ventilation port. In such embodiment, the gas monitoring port includes a luer lock.

In another embodiment of the invention, there is provided a nasal ventilation mask having an exterior opening under a nose region in the mask, over the patient's lip region, that allow gases expelled orally to be scavenged and ported to a scavenger device, said mask optionally further including a Scavenger line for diverting a portion of the expelled gas to be monitored for end-tidal $CO_2$, and, wherein a connector preferably is provided at point where the end-tidal $CO_2$ monitoring line intercepts the Scavenger line, effectively diverting the gas flow, resulting in a positive pressure relative to the end-tidal $CO_2$ line whereby to permit gasses to be sampled from the scavenger line.

In such embodiment, the mask may further comprise an anesthesiologist controlled 2-way, 3 port valve permitting an anesthesiologist to switch between separately monitoring nasal and oral expulsions of end-tidal $CO_2$ or monitoring them simultaneously when the valve is open to both, wherein, when the Oral end-tidal $CO_2$ monitoring port is chosen, the end-tidal $CO_2$ monitoring line preferably also serves to scavenge other ventilation gasses during anesthesia.

The present invention also provides a nasal ventilation mask having tabs or eyelets for attaching the mask anteriorly with the mask anchor, or posteriorly with a traditional anesthesia mask strap, said mask further optionally characterized by one or both of the following features:

(a) allowing only one combined anterior-posterior head strap to be attached, where the posterior head strap can attach to the mask alone, or can attach to the mask and then to a surface, which will prevent movement of the patient's head and/or neck; or (b) securing the patient's head with a head strap to the support surface, where the patient's head will stay in a desired position and the support surface will stay in the desired position when the provider changes the head and/or neck angles.

In yet another embodiment of the invention there is provided a nasal mask characterized by one or more of the following features:

(a) wherein the mask is usable as an oxygen transport mask or as a Ventilation mask providing $O_2$ and anesthesia gases and for monitoring end-tidal $CO_2$ simultaneously;

(b) having ports for monitoring end-tidal $CO_2$ via one or more ports, that can be used for CPAP pre-operatively, intra-operatively, and post-operatively;

(c) having ports for monitoring end-tidal $CO_2$ via one or more ports, that can be connected to a resuscitator bag in such a way that the patient's mouth and airway are not obstructed by the resuscitator bag to allow for direct laryngoscopy and intubation;

(d) wherein the mask is attachable anteriorly with a mask anchor, or posteriorly with a traditional anesthesia mask strap; and (e) having an $O_2$ port for introducing oxygen into the mask, a ventilation port and a gas monitoring attachment integral to or attached to the ventilation port, wherein the gas monitoring port preferably includes a luer lock The present invention also provides an anesthesia mask having a built in scavenger system for collecting anesthetic gases that leak out around the mouth and/or nose.

In yet another embodiment, the present invention provides a chin strap for application to the submental space, attached to a nasal mask, for applying pressure to force a wearer's tongue against the soft palate and induce an obstruction of the retro-glossal space, whereby to reduce or prevent leakage of gases out of the patient's mouth and allow the patient to breath out of the nose, wherein the chin strap also has the ability to release pressure, if needed, during exhalation to prevent an expiratory obstruction.

In another aspect the present invention provides an improved CPR mask for mouth-to-mouth and/or nose-to-mouth resuscitation and includes a $CO_2$ absorber that eliminates re-breathing of rescuer or provider exhaled $CO_2$ by the victim. More particularly, the present disclosure provides a CPR mask which includes a $CO_2$ filter or absorber built into the mask or mask inlet for absorbing $CO_2$ being exhaled by the rescuer or provider.

That is to say, there is provided a CPR mask for mouth-to-mouth and/or nose-to-mouth resuscitation, comprising a body shaped to cover the nose and/or mouth of a victim, said mask including a $CO_2$ absorber for eliminating at least in part rescuer exhaled $CO_2$ delivered to the victim.

In one embodiment, the $CO_2$ absorber is coated on an inside surface of the mask.

In another embodiment, the mask includes a ventilation tube, wherein the $CO_2$ absorber is located in the ventilation tube.

In still another embodiment the mask includes one-way valve and/or straps for holding the mask to the head of the victim.

In one embodiment the mask includes a compliant periphery to conform to the face of a victim. In such embodiment, the periphery may include a soft, compliant air bladder, or resiliently deformable foam cushion.

In yet another embodiment, the mask includes a biological filter incorporated into the inside of the mask, or incorporated into the ventilation tube.

In still yet another embodiment of the invention, there is provided a CPR mask as above described, further characterized by one or more of the following features:

(a) including a one-way valve;

(b) including straps for holding the mask to the head of the victim; and (c) wherein the mask further includes a compliant periphery to conform to the face of a wearer, wherein the periphery preferably includes a soft, compliant air bladder or a resiliently deformable foam cushion.

BRIEF DESCRIPTION OF THE DRAWINGS

Further features and advantages of the present invention will be seen from the following detailed description, taken in conjunction with the accompany drawings, wherein.

DETAILED DESCRIPTION OF THE DRAWINGS

Figures 1A, 1B:
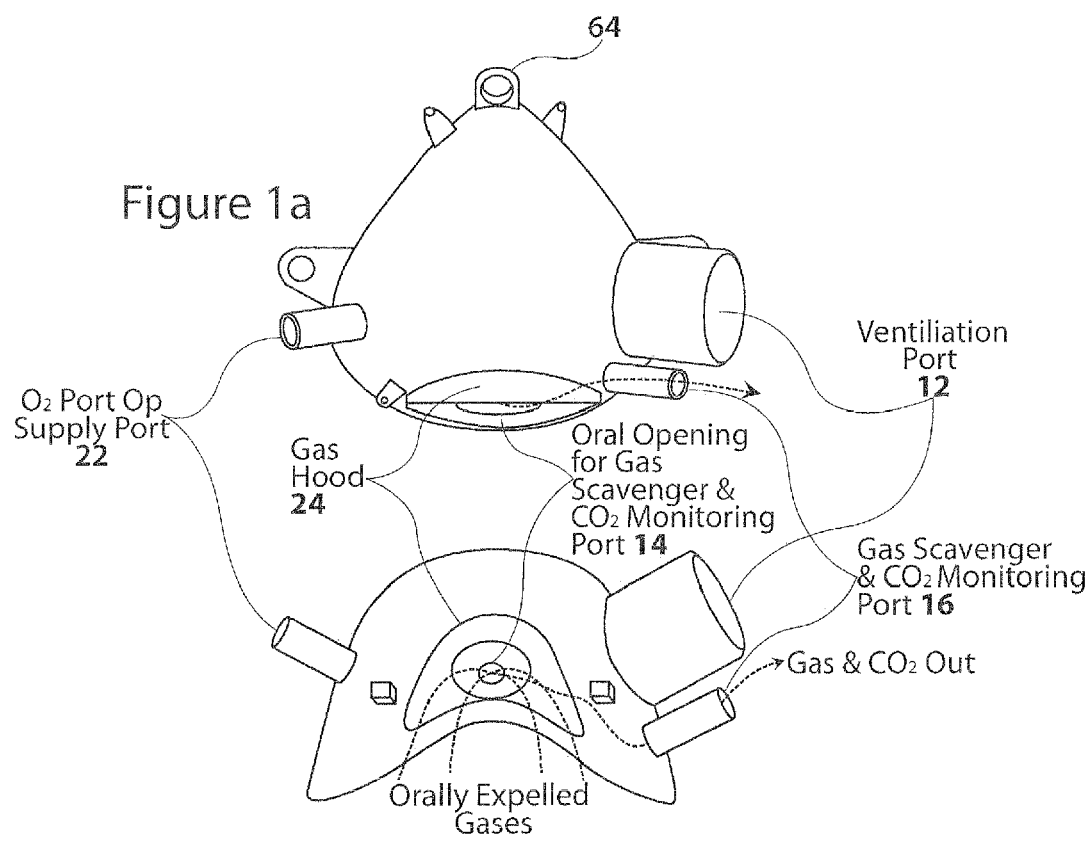
FIGS. 1a and 1b are front view and top views of a nasal ventilation mask in accordance with the first embodiment of the present invention.

A nasal ventilation mask 10 in accordance with a first embodiment of the present invention is illustrated in FIGS. 1a and 1b. Optimally it contains 4 gas openings, but can contain less or more than four as well. The first is the ventilation port 12 that supplies $O_2$ and other gasses either during anesthesia or for NIPPV in critically ill patients and allows for any end-tidal $CO_2$ that is expelled nasally to be retrieved from the patient. The second is an Oral opening 14 under the nose but isolated from the nasal cavity created by the mask over the patient's nose. The purpose of opening 14 is for scavenging anesthesia gases and end-tidal $CO_2$ that are expelled orally from the patient. In addition to reducing or eliminating anesthetic gasses from entering the Operating Room and becoming a hazard, it allows for the end-tidal $CO_2$ expelled from the patient's lungs and escaping orally to be monitored. The third opening is the Gas Scavenging/end-tidal $CO_2$ port 16 that is connected to the opening by a channel 18 inside the mask (see FIG. 2) that is isolated from the nasal cavity. The Gases, including any expelled end-tidal $CO_2$, leave the mask through port 16 and are guided by a tube 20 to a gas scavenging filter and end-tidal $CO_2$ monitor 32 (see FIG. 3) that samples gas from the gas scavenging line. The fourth opening is an $O_2$ port 22 that is capped off during anesthesia, but may be connected to an $O_2$ source (not shown) either pre-operation, intra-operation, or post-operation. When $O_2$ is supplied, the Ventilation tube is detached from the ventilation port 12 so that end-tidal $CO_2$ and be expelled nasally. A gas hood 24 located under the nose around the oral opening 14 extends beyond the mask as shown. It is optionally included in order to extend the influence of the Oral Opening 14 in the mask in order to contain a greater percentage of the expelled gases from the patient.

The mask also includes three eyelets or tabs 60, 62, 64, or four eyelets or tabs 66 68, 70, 72 (FIG. 7) for attaching a chin strap or head strap, as described below, or for attaching straps to the operating table in accordance with the teachings of our application PCT/US14/44934 or our PCT application PCT/US15/34277.

Figure 2:
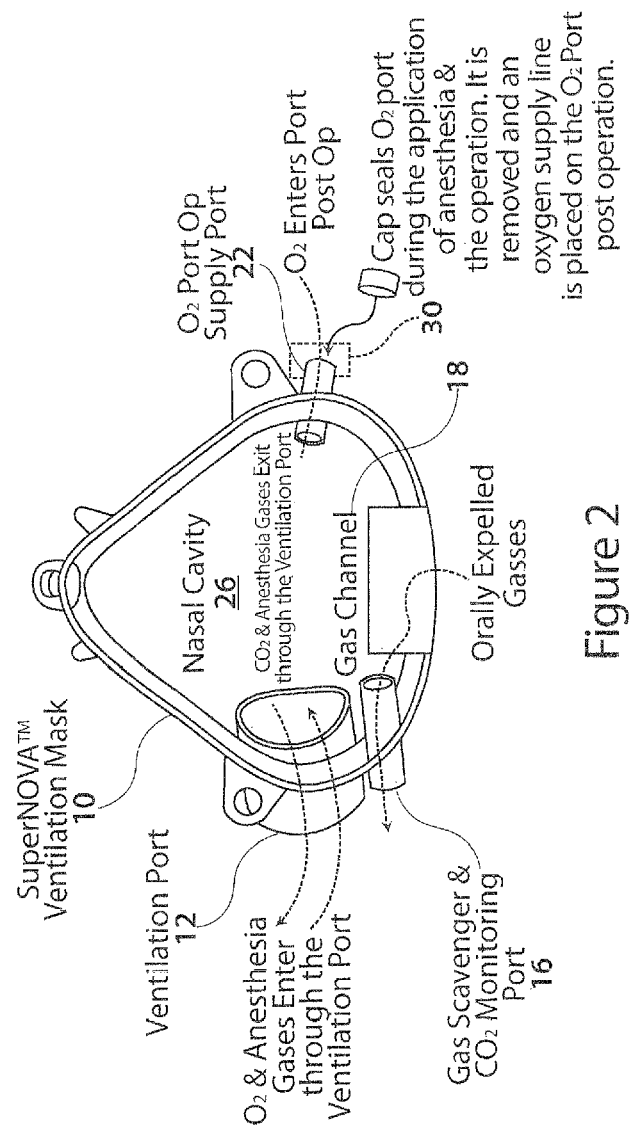
FIG. 2 is an inside view of the FIG. 1a ventilation mask.

An interior view of the nasal ventilation mask 10 of the present invention is illustrated in FIG. 2. The ventilation port 12 and $O_2$ port 22, are connected to the nasal cavity 26. Orally expelled gases travel from the Oral opening 14 on the outside of the mask through Gas Channel 18 and out the Gas Scavenger & end-tidal $CO_2$ monitoring port 16 on to the Scavenger device and end-tidal $CO_2$ monitor. The Gas channel 18 separates the Nasal cavity 26 created by the ventilation mask over the nose and the Oral regions of the patient.

When $O_2$ or $O_2$ and anesthesia gasses and are being supplied to the patient, they travel to the nasal cavity 26 through a ventilation circuit 28 attached to the ventilation port 12, and a cap shown in phantom at 30, seals the $O_2$ port. Post operation, the cap 30 can be removed from the $O_2$ port 22 and an $O_2$ line attached to the port, supplying $O_2$ to the patient. The ventilation circuit 28 is removed from the ventilation port 12 and the nasal cavity 26 is open to the atmosphere where end-tidal $CO_2$ can be expelled nasally.

Figure 3A:
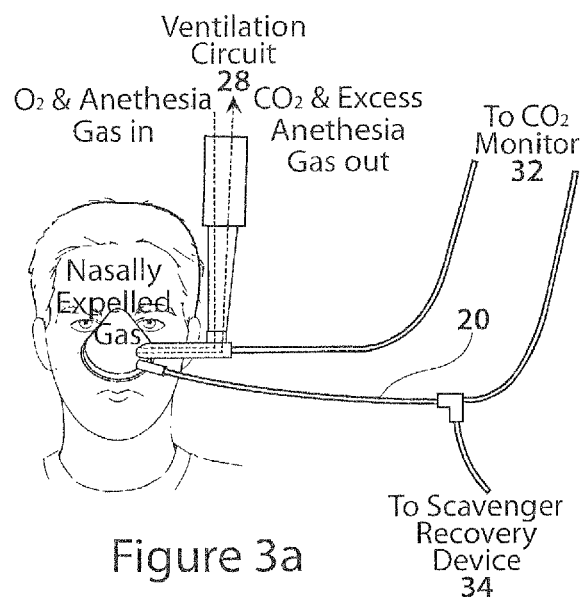
FIGS. 3a and 3b are plan views showing the ventilation mask in accordance with the present invention on a patient's head.
Figure 3B:
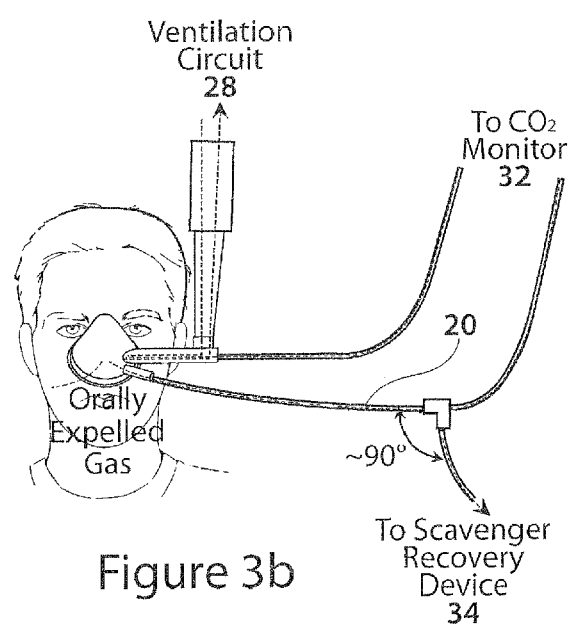

The gas circuit for both the Nasal Mask Ventilation/end-tidal $CO_2$ monitor Oral Gas Scavenger/end-tidal $CO_2$ monitoring lines are illustrated in FIGS. 3a and 3b. FIG. 3a shows nasal gas flow from the Nasal cavity 26 connected to the Ventilation Circuit 28 and to the end-tidal $CO_2$ monitoring equipment 32. FIG. 3b shows the orally expelled gasses entering the Oral opening and flowing through the Gas Scavenger line to a recovery device 34 and the associated line that is connected to the scavenger line and flows to the end-tidal $CO_2$ monitoring equipment. Note that the opening to the scavenger line should be positioned approximately 90° to the scavenger gas flow in order for the local pressure to be higher than it would be if the opening were perpendicular to the gas flow. If it were perpendicular, a negative pressure would prevent the end-tidal $CO_2$ monitoring line from being able to sample the flow due to the negative pressure gradient.

Figure 4A:
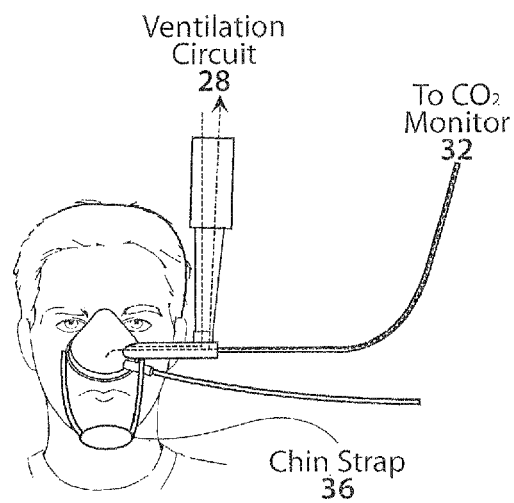
FIGS. 4a and 4b are views similar to FIGS. 3a and 3b showing a chin strap attached to the mask.
Figure 4B:
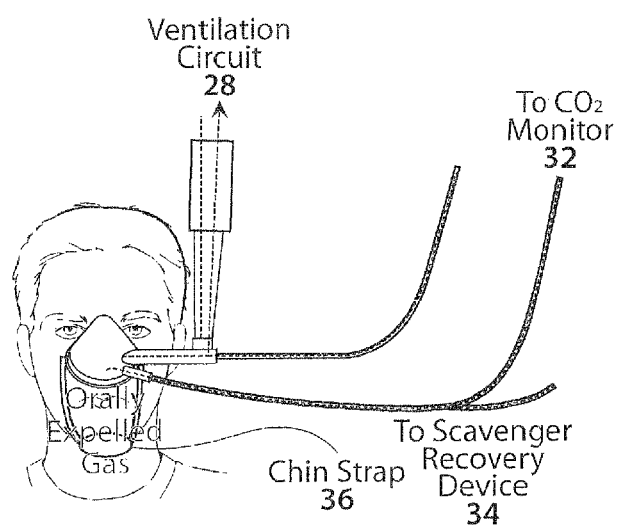

Referring also to FIGS. 4a and 4b, a chin strap 36 also can be applied to the submental space, attached to the nasal mask 10, and apply a pressure to force the tongue against the soft palate and induce an obstruction of the retro-glossal space, which will help prevent any leak of gases out of the patient's mouth and allow the patient to breath out of the nose. The chin strap 36 also has the ability to release pressure, if needed, during exhalation to prevent an expiratory obstruction and allow end-tidal $CO_2$ and other gases to be released out the mouth.

Figure 5A:
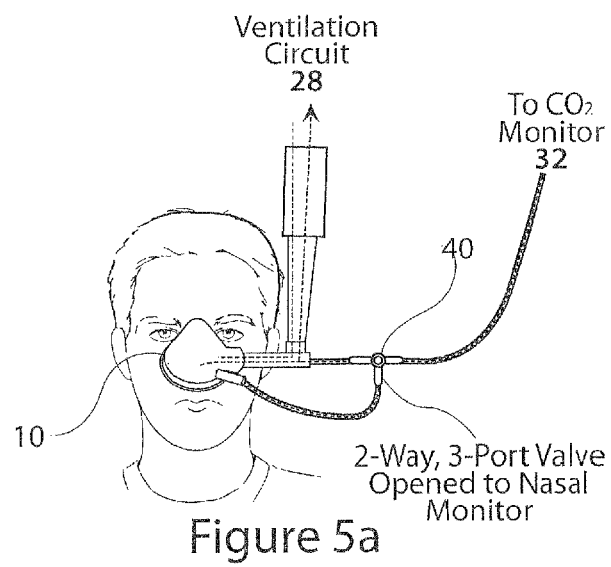
FIGS. 5a and 5b show an alternative configuration of the nasal mask with an end-tidal $CO_2$ monitor in accordance with the present invention.
Figure 5B:
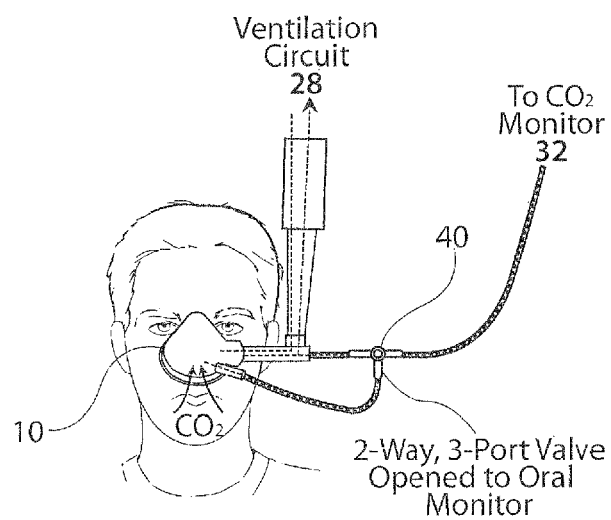

In an alternate configuration, the gas circuit for both the Nasal Mask Ventilation and end-tidal $CO_2$ monitoring are illustrated in FIGS. 5a and 5b. The figure shows a 2-Way, 3 Port valve 40 that connects the Nasal circuit to the end-tidal $CO_2$ monitoring equipment. The anesthesiologist decides which region, the nasal, oral region, or both simultaneously, should be monitored for end-tidal $CO_2$.

Figure 6:
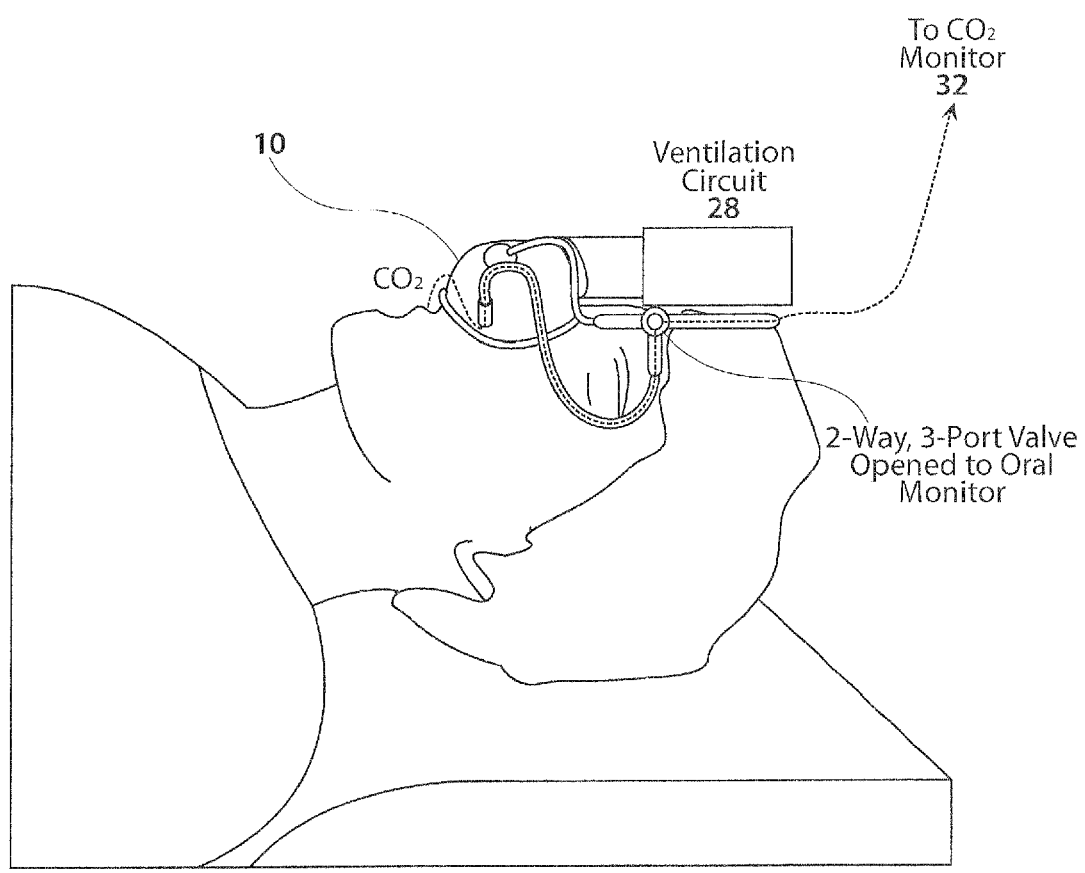
FIG. 6 is a side elevational view of an alternative configuration of nasal mask ventilation system in accordance with the present invention.

A side view of the alternate configuration for the nasal mask ventilation and monitoring end-tidal $CO_2$ expulsion from the oral airway is illustrated in FIG. 6. Note the 2-Way, 3 Port valve 40 has been turned in the direction of the mouth for sampling end-tidal $CO_2$.

The nasal ventilation mask also allows only one combined anterior-posterior head strap to be attached, where the posterior head strap can attach to the mask alone, or can attach to the mask and then to a surface, which will prevent movement of the patient's head and/or neck. By securing the patient's head with the head strap to the support surface, the patient's head will stay in the desired position and the support surface will stay in the desired position when the provider changes the head and/or neck angles.

Figure 7:
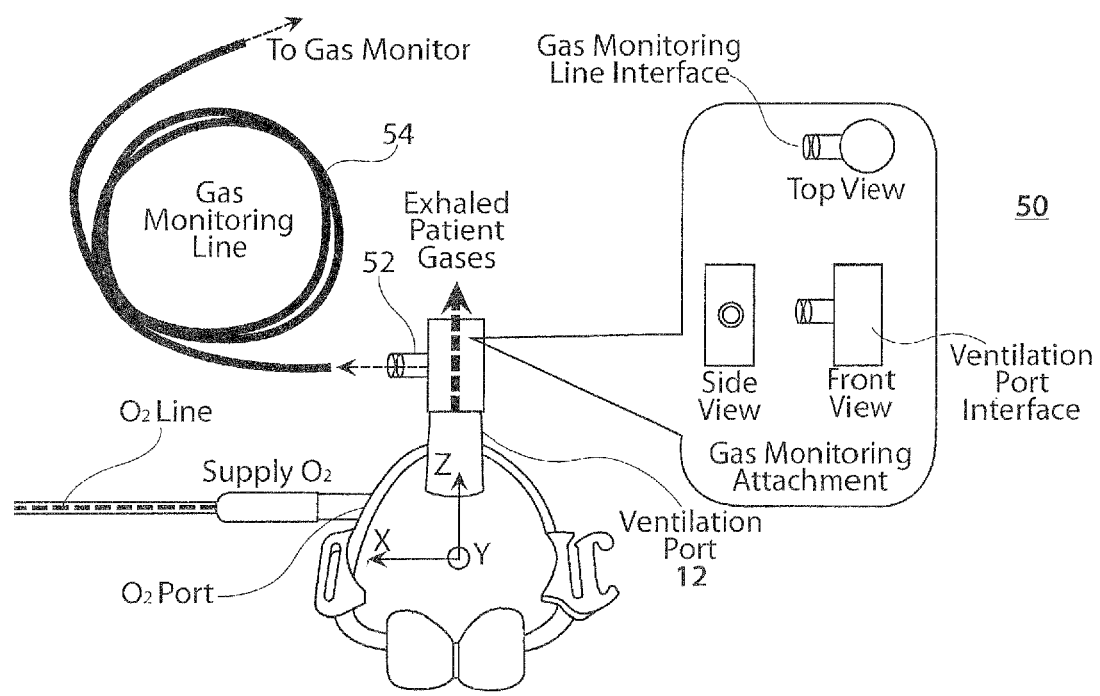
FIG. 7 is a plan view of an alternative embodiment of nasal ventilation mask with a $CO_2$ monitor in accordance with the present invention.

FIG. 7 illustrates yet another embodiment of the invention, in which a patient is being provided oxygen via an $O_2$ line connected to the $O_2$ port on the ventilation mask. The exhaled gasses are exhausted to the atmosphere via the ventilation port 12 as illustrated in FIG. 7. If the patient is unconscious due to anesthesia, there is a desire to assure that the $CO_2$ is being exhaled. This can be accomplished by adding a "T-Shaped" gas monitoring attachment 50 that slides onto the mask ventilation port 12. The main body of the attachment 50 which is tubular in shape allows exhaled gasses to be exhausted to the atmosphere. To the side of the attachment is a tubular opening 52, nominally at a 90° angle off to the side. The end of this opening 52 can have a luer lock or any other kind of securing connection. Exhaled gas from the main flow can be sampled through this opening if a gas monitoring line 54 connected to a gas monitor is attached to the gas monitoring line interface.

Figure 8:
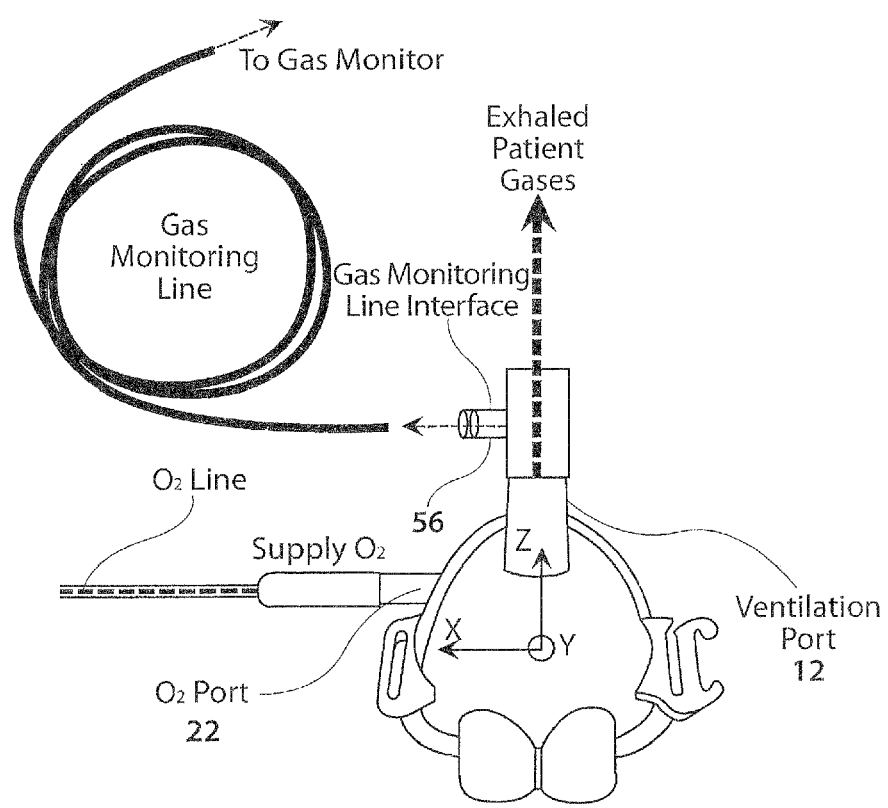
FIG. 8 is a plan view of yet another alternative configuration of nasal mask with a $CO_2$ monitor in accordance with the present invention.

An alternative approach for accomplishing the same gas sampling feature is illustrated in FIG. 8. In this embodiment, the gas monitoring line interface is an integral element of the mask ventilation port 12. In this configuration, $O_2$ flows into the $O_2$ port via a supply line and the exhaust gases are passed to the atmosphere via the ventilation port 12. The side of the ventilation port 12 is a tubular opening 56, nominally at 90° angle off to the side. The end of this opening can have a luer lock or any other kind of securing connection. Exhaled gas from the main flow can be sampled through this opening if a gas monitoring line connected to a gas monitor is attached to the gas monitoring line surface.

Figure 9:
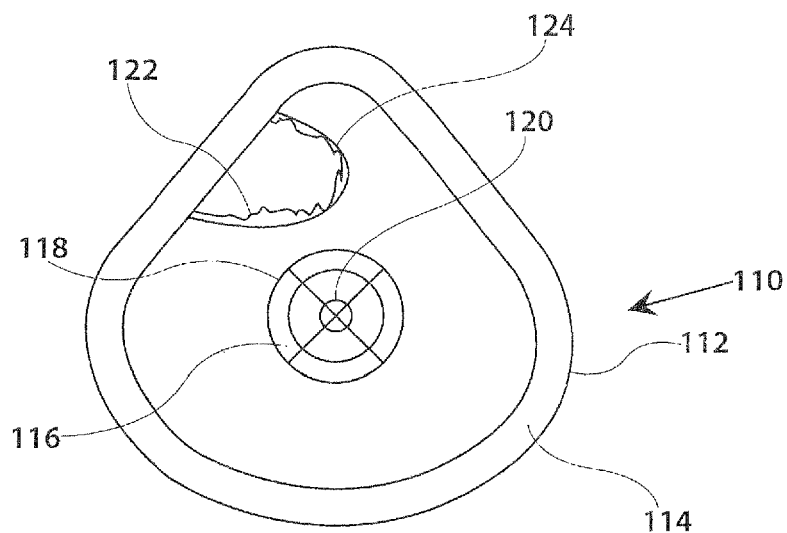
FIG. 9 is a view, in partial cross-section of a CPR mask in accordance with the first embodiment of the present invention.

Referring to FIG. 9, there is shown a first embodiment of a CPR mask in accordance with another aspect of our invention, designated 110, to affect rescue breathing, mouth-to-mouth resuscitation or any other CPR procedure requiring emergency breathing assistance. Mask 110 is shaped to cover the nose and/or mouth of a victim, and includes a soft and compliant periphery 112 to conform to the face of a victim upon application of moderate force to obtain a tight-fitting mask seal. Typically the periphery 112 of the mask includes a soft, compliant air bladder 114 or resiliently deformable foam cushion or the like.

A ventilation tube 116 is attached to an integral inlet port 118 protruding from the mask through which air may be supplied by the rescuer by exhaling into the tube. Ventilation tube 116 or inlet port 118 typically includes a one-way valve 120 that permits air to enter the mask through tube 116. Ventilation tube 116 and its associated valve 120 may be formed integrally with the port 118, or may be a replaceable, disposable element or package. (FIG. 10).

The inside surface 122 of mask 110 is coated in part by a $CO_2$ absorbing material such as activated carbon or a zeolite. Also, certain minerals such as serpentinite advantageously may be employed. Typically, these materials are sorted to optimal size and encased in a filter material 124 bound to the inside surface 122 of the mask 110. Alternatively, the inside surface 122 of the mask 110 may be coated with a $CO_2$ absorbing polymer such as polyethylenimine containing fumed silica or the like as reported in Scientific American, Jan. 6, 2012, page 33.

Figure 10:
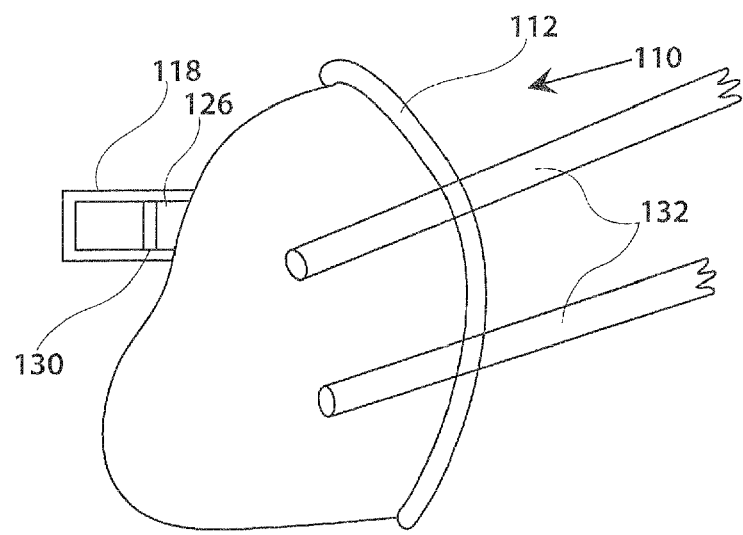
FIG. 10 is a side elevational view of a second embodiment of a CPR mask in accordance with the present invention.

Alternatively, as shown in FIG. 10, a $CO_2$ filter 126 containing $CO_2$ absorbing material may be incorporated into ventilation tube 116.

In use, the rescuer places the CPR mask 110 over the nose and/or mouth of a victim to initiate emergency ventilation of the victim. The rescuer applies moderate force to obtain a substantially air-tight seal against the victim's face, and ventilation is then supplied by the rescuer by exhaling into the ventilation tube 116. While the exhaust from the rescuer contains $CO_2$, most of the $CO_2$ will be removed by the $CO_2$ filter material.

Mask 110 may be formed in different sizes, for example, adult size, youth size and child size, to accommodate different size faces. A feature and advantage of the CPR mask of the present invention is that significantly reduces the amount of $CO_2$ administered to the victim. Also, the mask helps to protect both victim and rescuer in an emergency situation by preventing transfer of disease.

Various changes may be made in the above invention without departing from the spirit and scope thereof. For example, a biological filter (shown in phantom at 130 in FIG. 10) also may be incorporated into the mask or the ventilation tube 116. Additionally, the mask may include straps 132 for strapping the mask to the victim's head, thus freeing the rescuer from having to press the mask against the victim's face. Still other changes are possible.

What is claimed is:

1. A nasal ventilation mask having a body defining a nasal cavity having an interior configured to cover a patient's nose while leaving a patient's mouth uncovered, the mask having an O2 port, a ventilation port, and an end-tidal CO2 port, the O2 port fluidly coupled to the nasal cavity for introducing oxygen into the nasal cavity, the ventilation port fluidly coupled to the nasal cavity for directing a gas toward or away from the nasal cavity, and the end-tidal CO2 port fluidly coupled to an exterior opening under a nose region of the mask, adapted to overlie a patient's lip region and isolated from the nasal cavity, wherein the end-tidal CO2 port is configured to couple with a monitoring line, and the ventilation port is configured to couple with a ventilation line that is different than the monitoring line, and the exterior opening is adapted to scavenge gases expelled orally by a wearer.

2. The mask of claim 1, wherein the mask is adapted for use as an oxygen transport mask, or as a ventilation mask providing O2 and anesthesia gases.

3. The mask of claim 1, wherein the mask is adapted for CPAP pre-operatively, intra-operatively, and/or post-operatively.

4. The mask of claim 1, wherein the mask is adapted for connection to a resuscitator bag such that a patient's mouth and airway are not obstructed by the resuscitator bag, to allow for direct laryngoscopy and intubation.

5. The mask of claim 1, wherein the mask comprises a gas channel inside the nasal cavity, wherein the gas channel fluidly couples the end-tidal CO2 port to the exterior opening and is configured to isolate orally expelled gases from a rest of the cavity.

6. The mask of claim 1, wherein the mask comprises a gas monitoring attachment.

7. The mask of claim 6, wherein the gas monitoring attachment is integral to or attached to the ventilation port.

8. The mask of claim 1, further comprising an anesthesiologist controlled 2-way, 3 port valve permitting an anesthesiologist to switch between separately monitoring nasal and oral end-tidal CO2, or simultaneously monitoring nasal and oral end-tidal CO2, wherein when oral end-tidal CO2 monitoring is chosen, ventilation gases expelled orally by the patient are also monitored.

9. The mask of claim 1, wherein the mask comprises a scavenger line configured to for diverting at least a portion of the scavenged gas to an end-tidal CO2 monitor.

10. The mask of claim 9, wherein a connector is provided where the monitoring line intercepts the scavenger line, diverting gas flow, resulting in a positive pressure relative to the monitoring line, to permit gases to be sampled from the scavenger line.

11. A nasal ventilation mask comprising a body defining a nasal cavity having an interior configured to cover a patient's nose while leaving a patient's mouth uncovered, the mask having a first port fluidly coupled to the nasal cavity and configured for introducing oxygen into the nasal cavity, a second port fluidly coupled to the nasal cavity and configured for directing a gas toward or away from the nasal cavity, and a third port fluidly coupled to an exterior opening under a nose region of the mask, wherein the exterior opening is isolated from the nasal cavity and is adapted to overlie a patient's lip region, and the third port is configured to couple with a monitoring line, the second port is configured to couple with a ventilation line that is different than the monitoring line, and the exterior opening is adapted to scavenge gases expelled orally by a wearer.

12. The mask of claim 11, wherein the mask comprises a gas channel inside the nasal cavity, wherein the gas channel fluidly couples the third port to the exterior opening.

13. The mask of claim 11, wherein the mask comprises a gas monitoring attachment.

14. The mask of claim 13, wherein the gas monitoring attachment is integral to or attached to the second port.

15. The mask of claim 11, further comprising an anesthesiologist controlled 2-way, 3 port valve permitting an anesthesiologist to switch between separately or simultaneously monitoring any of the first, second, and third ports.

16. An anesthesia mask having a body defining a nasal cavity having an interior configured to cover a patient's nose while leaving a patient's mouth uncovered, the anesthesia mask having a first port, a second port, and a third port, and a scavenger system, the first port fluidly coupled to the nasal cavity and configured for introducing oxygen into the nasal cavity, the second port fluidly coupled to the nasal cavity and configured for directing a gas toward or away from the nasal cavity, and the third port coupled to an exterior opening under a nose region of the mask and adapted to overlie a patient's lip region, and the scavenger system configured for collecting anesthetic gases that may leak out around a mouth and nose of a patient, the scavenger system comprising the third port and a gas hood, the gas hood located under the nose region of the anesthesia mask and extending from an outer surface of the anesthesia mask around the exterior opening to enhance the collection of anesthetic gases around the patient's mouth, wherein the third port is configured to couple with a monitoring line, and the second port is configured to couple with a ventilation line that is different than the monitoring line.

17. The mask of claim 16, wherein the mask comprises a gas channel inside the nasal cavity, wherein the gas channel fluidly couples the third port to the exterior opening.

18. The mask of claim 16, wherein the mask comprises a gas monitoring attachment.

19. The mask of claim 18, wherein the gas monitoring attachment is integral to or attached to the second port.

20. The mask of claim 16, further comprising an anesthesiologist controlled 2-way, 3 port valve permitting an anesthesiologist to switch between separately or simultaneously monitoring any of the first, second, and third ports.

* * * * *